Sept. 18, 1973 R. H. McCOLLEY Plant Pat. 3,396
DISTINCT VARIETY OF PHILODENDRON PLANT
Filed April 10, 1972
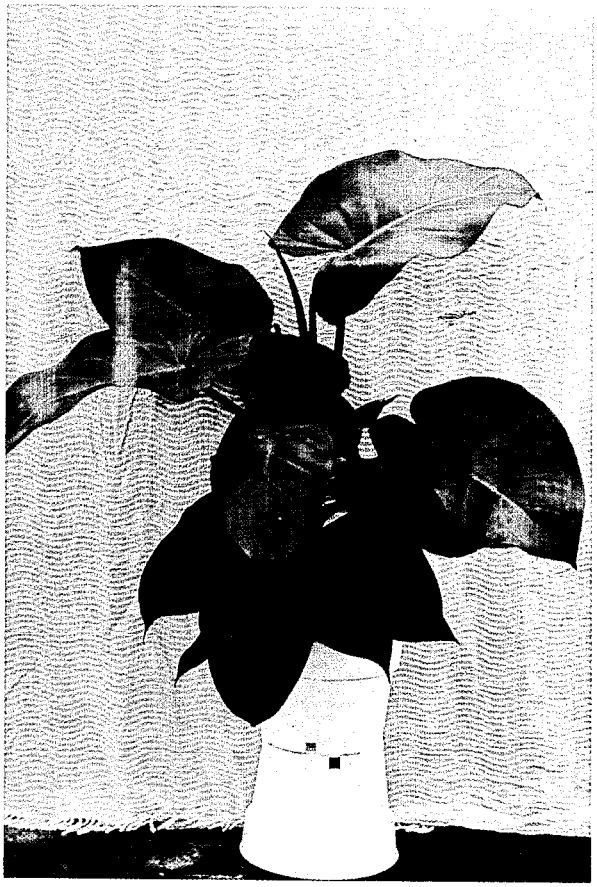

United States Patent Office

Plant Pat. 3,396
Patented Sept. 18, 1973

3,396

DISTINCT VARIETY OF PHILODENDRON PLANT

Robert H. McColley, P.O. Box 17126,
Orlando, Fla. 32810

Filed Apr. 10, 1972, Ser. No. 242,844
Int. Cl. A01h *5/00*
U.S. Cl. Plt.—88 1 Claim

ABSTRACT OF THE DISCLOSURE

The disclosure hereof is of a Philodendron plant of compact form, having leathery leaves which in their immature stage are of a greyish brown, and maturing become olive grey, producing a general two-color effect which in dark conditions is almost black.

DESCRIPTION OF THE INVENTION

My present invention comprises a new and distinct variety of Philodendron plant which is the result of selfing a seedling selected from a cross of the *Philodendrons wendlandii, hastatum, erubescens, imbe,* and an unnamed species, and in turn selfing a seedling of this cross.

I have conducted an extensive program of hybridizing, a good deal of which has been directed to the endeavor to develop a tough, leathery Philodendron which is compact, an excellent keeper and as nearly black as possible. This Philodendron of the instant invention is the closest approach which I have been able to develop to the present time.

My new variety has been asexually reproduced by single eye and tip cuttings in the vicinity of Orlando, Fla., and has been found to retain its distinctive characteristics through successive asexual reproduction.

The new variety has been exposed to adverse conditions in various sections of the United States, including California, Illinois, New Jersey and Florida, and has been able to provide superior foliage and thus a superior foliage plant in every instance.

My new variety is distinctive from other Philodendrons in cultivation and is not described by Graf, Bailey or Das Pflanzenreich. It is therefore only compared with the patented Philodendron of Patent No. 3034 to indicate differences residing therebetween.

My new variety is visually distinguished by the following characteristics of the leaf, including an ovate form with cordate leaf base and a cuspidate leaf tip.

The leaves include pinnate veination, having smooth midribs with sunken veins.

An undulate surface prevails with the width of the leaves being about three-quarters of their length.

The plant itself is one which grows in very dense form, having alternate petioles which are from one-half to two-thirds the length of the leaf.

The petioles are horizontal to semi-erect, and the leaves horizontal to slightly pendant with internodes ½" to 1½".

Probably one of the most distinctive aspects of the plant is that of the color of the leaves and the general impression created thereby, which leaves, petioles and stem are a greyish brown, appearing almost black in medium to low light intensity. As the leaves mature after a period of six months, for example, they turn to olive grey.

Certain of the physical characteristics of the plant of my new variety which are of value in the commercial field, are the fact that the plant will withstand extremely low light intensity and low soil moisture content for weeks. Actually a low humidity and high temperatures are not particularly troublesome to the keeping of the plants under virtually all conditions.

The leaves are very thick, rubbery and withstand bruising and dehydration without wilting.

The diseases to which the plant is resistant include bacterial soft rot and it is almost immune to "shot gun" fungus.

The aspect of the plant in respect to growth, is noticeably different from others and in its mature form, it is a very compact grower and does not require staking. The juvenile form of plant is a slow growing vine and makes an ideal totem pole.

Indoor growing of the plant is not harmful, since it retains its desired form and size longer than varieties currently available.

The following detailed specifications are based on observations made in my greenhouse in Orlando, Fla.

The accompanying drawing forming a part of this disclosure, shows a typical plant of my new variety, the colors being as nearly true as possible with color illustrations of this type. Color references are made to the Nickerson Color Fan published by Munsell Color Company, with observations being recorded by day-light illumination under vinyl of not more than 30% shade.

(I) Form characteristics:

| | |
|---|---|
| (1) Leaf shape: | |
| (a) Mature | Ovate. |
| (b) Immature | Ovate. |
| (c) Tip | Cuspidate. |
| (d) Base: | |
| (1) Mature | Cordate. |
| (2) Immature | Obtuse. |
| (e) Displacement | Undulate. |
| (f) Margin | Entire. |
| (g) Veination | Smooth midrib; sunken veins. |
| (2) Leaf attachment | Stalked. |
| (3) Leaf arrangement | Alternate; horizontal to slightly pendant. |
| (4) Petiole | Short; horizontal to semi-erect. |
| (5) Stem | Short; heavy internodes ½" to 1½". |
| (6) Overall appearance | Dense. |

(II) Size characteristics of typical commercial size:

| | Inches |
|---|---|
| (1) Leaf itself: | |
| (a) Width-widest point | 5–10 |
| (b) Width-1" from tip | 1½ |
| (c) Length | 8–14 |
| (d) Thickness | .016 |
| (2) Petiole: | |
| (a) Length | 4½–9 |
| (b) Diameter (center) | ¼–½ |
| (c) Internode spacing | ¼–1 |
| (d) Stem diameter | ⅜–1¼ |

(III) Color characteristics:

| | |
|---|---|
| (1) Leaf (mature): | |
| (a) Top | 10Y 3/1 |
| (b) Bottom | 10YR 3/1 |
| (2) Leaf (immature): | |
| (a) Top | 7.5YR 3/2 |
| (b) Bottom | 2.5YR 3/3 |
| (3) Leaf veination: | |
| (a) Midrib | 10R 3/4 |
| (b) Veins | 10R 3/4 |
| (4) Stem, darker | 2.5R 3/7 |
| (5) Petiole, darker | 2.5R 3/7 |

I claim:

1. A new and distinct variety of Philodendron plant, substantially as herein disclosed, characterized as to novelty by its compact form, tough, leathery leaves, excellent keeping qualities and slow growth indoors, the greyish brown color of immature leaves and olive grey color of those leaves which are more mature.

No references cited.

ROBERT E. BAGWILL, Primary Examiner